(12) United States Patent
Hamano et al.

(10) Patent No.: US 9,872,660 B2
(45) Date of Patent: Jan. 23, 2018

(54) MEDICAL DIAGNOSTIC IMAGING SYSTEM

(71) Applicant: Konica Minolta, Inc., Chiyoda-ku, Tokyo (JP)

(72) Inventors: Masaya Hamano, Tokyo (JP); Akira Kurahashi, Hachioji (JP); Norihiro Matsusaka, Hino (JP); Tomoyasu Yokoyama, Tsurugashima (JP); Mitsuharu Kitamura, Tokyo (JP); Satoshi Nishino, Sayama (JP)

(73) Assignee: KONICA MINOLTA, INC., Tokyo (JP)

( * ) Notice: Subject to any disclaimer, the term of this patent is extended or adjusted under 35 U.S.C. 154(b) by 100 days.

(21) Appl. No.: 14/681,609

(22) Filed: Apr. 8, 2015

(65) Prior Publication Data
US 2015/0282780 A1    Oct. 8, 2015

(30) Foreign Application Priority Data

Apr. 8, 2014  (JP) .................................. 2014-079211

(51) Int. Cl.
*A61B 6/00* (2006.01)
*A61B 6/04* (2006.01)

(52) U.S. Cl.
CPC ............ *A61B 6/484* (2013.01); *A61B 6/0407* (2013.01); *A61B 6/4035* (2013.01); *A61B 6/4291* (2013.01); *A61B 6/488* (2013.01); *A61B 6/505* (2013.01); *A61B 6/5205* (2013.01)

(58) Field of Classification Search
CPC ... A61B 6/0407; A61B 6/4035; A61B 6/4291; A61B 6/488; A61B 6/505; A61B 6/5205
See application file for complete search history.

(56) References Cited

U.S. PATENT DOCUMENTS

| | | | | |
|---|---|---|---|---|
| 6,330,572 B1* | 12/2001 | Sitka | ................. | G06F 17/30082 707/608 |
| 2007/0006322 A1* | 1/2007 | Karimzadeh | ......... | G06F 19/323 726/27 |
| 2012/0041785 A1* | 2/2012 | Tsunomori | ........... | A61B 6/5235 705/3 |
| 2012/0140882 A1* | 6/2012 | Iwakiri | ................ | A61B 6/4233 378/62 |
| 2012/0163554 A1* | 6/2012 | Tada | .................... | A61B 6/4035 378/154 |
| 2013/0201198 A1* | 8/2013 | Nagatsuka | ............. | A61B 6/463 345/581 |
| 2013/0308750 A1* | 11/2013 | Ishii | ..................... | A61B 6/4233 378/36 |

FOREIGN PATENT DOCUMENTS

| | | |
|---|---|---|
| JP | 2008200359 A | 9/2008 |
| WO | 2011033798 A1 | 3/2011 |
| WO | 2011142157 A1 | 11/2011 |

\* cited by examiner

*Primary Examiner* — David E Smith
(74) *Attorney, Agent, or Firm* — Cantor Colburn LLP

(57) ABSTRACT

A medical diagnostic imaging system includes an X-ray Talbot imaging apparatus and an image processing apparatus to reconstruct one or more moire images produced in the X-ray Talbot imaging apparatus into a plurality of types of medical diagnostic images. The image processing apparatus classifies the medical diagnostic images generated based on the same moire image(s) into a group and outputs the group of medical diagnostic images as a unit to the outside.

4 Claims, 13 Drawing Sheets

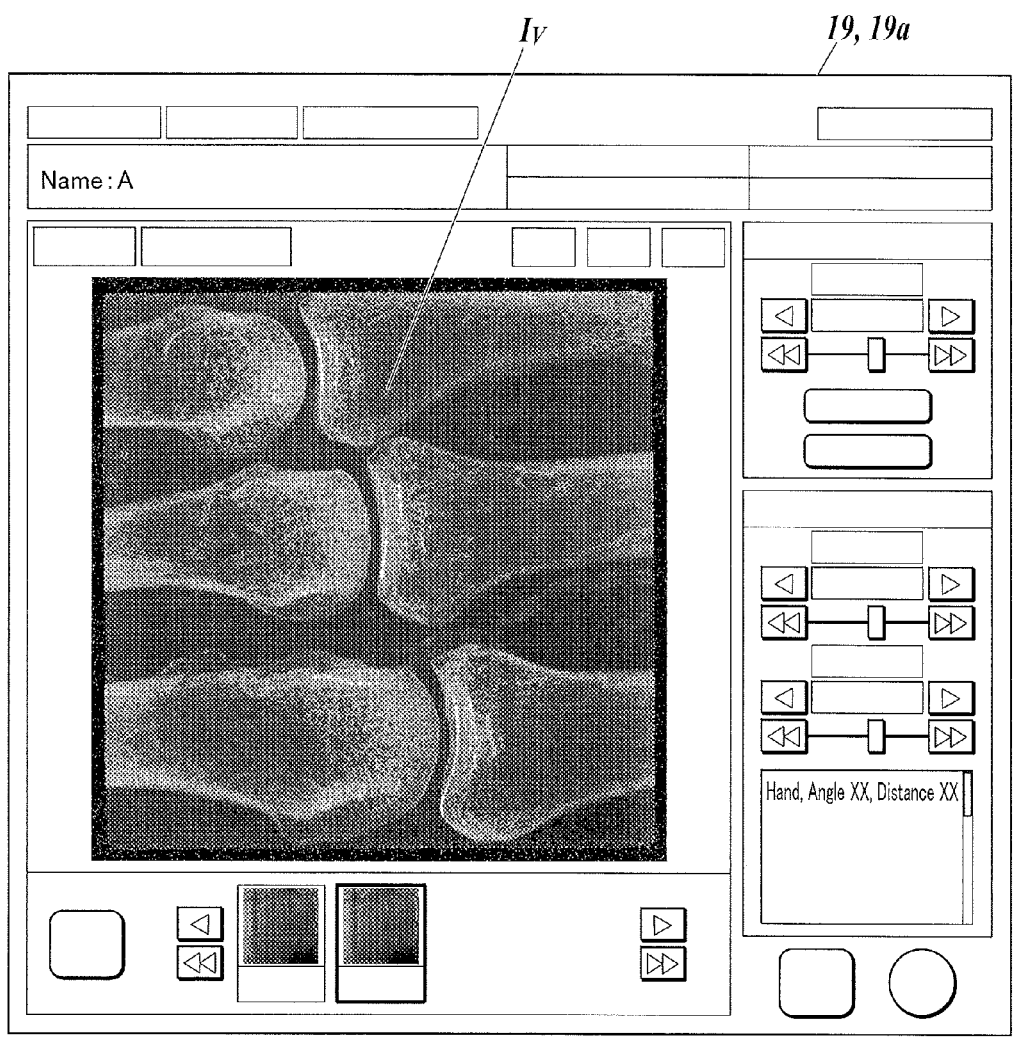

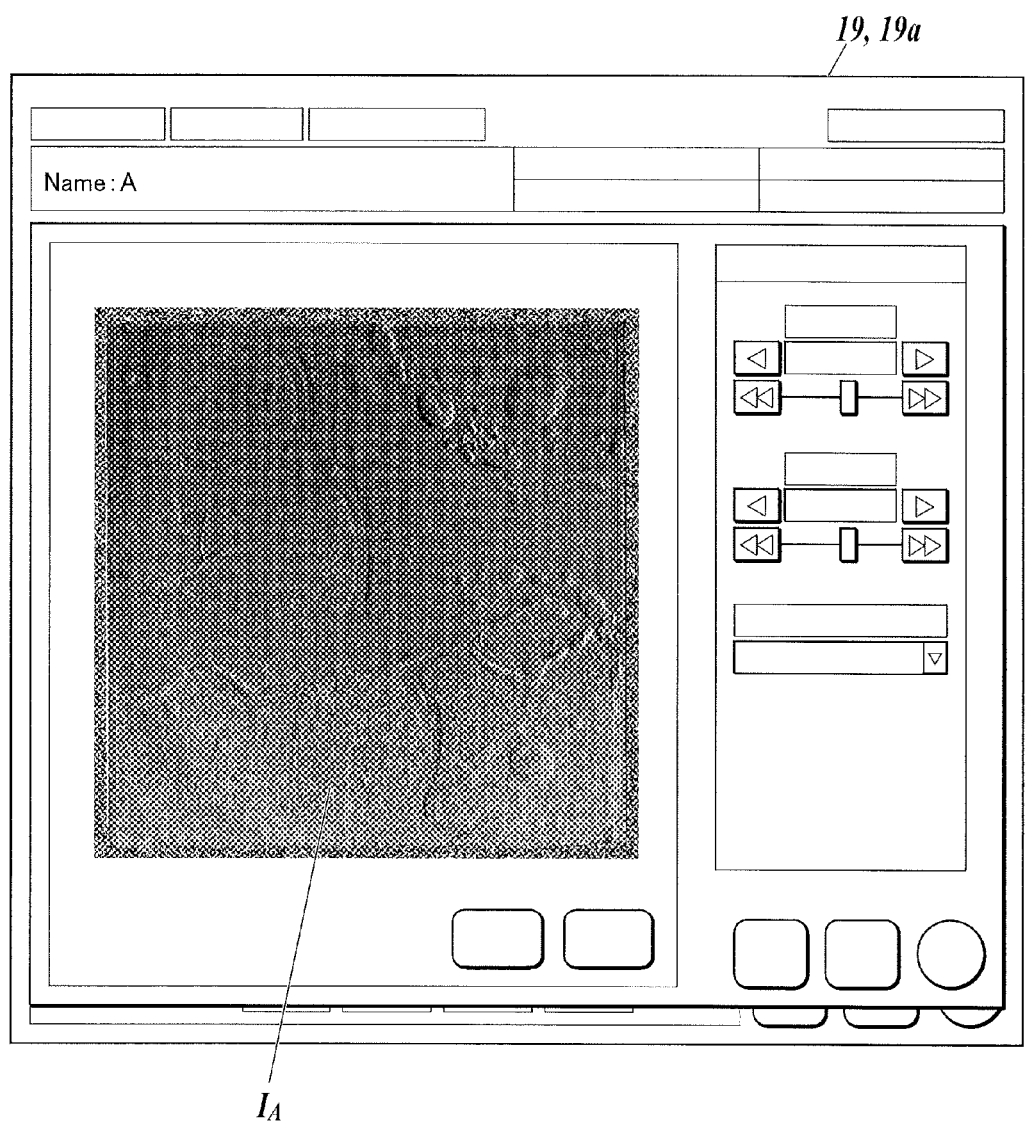

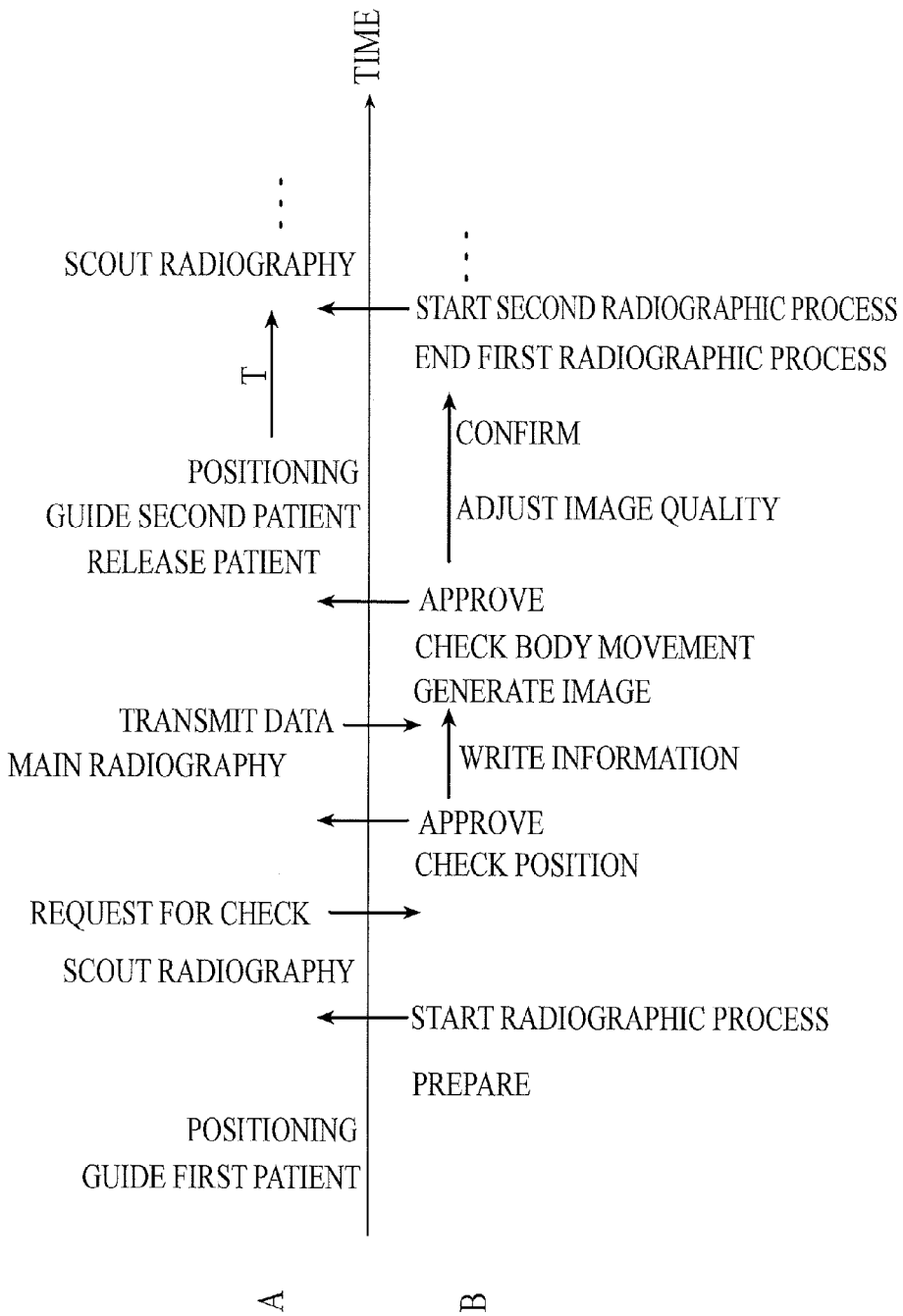

MEDICAL DIAGNOSTIC IMAGING SYSTEM

CROSS REFERENCE TO RELATED APPLICATIONS

The present invention claims priority under 35 U.S.C. §119 to Japanese Application No. 2014-079211 filed Apr. 8, 2014, the entire content of which is incorporated herein by reference.

BACKGROUND OF THE INVENTION

Field of the Invention

The present invention relates to a medical diagnostic imaging system including an X-ray imaging apparatus provided with a Talbot interferometer or a Talbot-Lau interferometer to generate a plurality of types of medical diagnostic images.

Description of Related Art

A variety of flat panel detectors (FPDs, or radiographic imaging devices) have been developed which include a two-dimensional array of conversion elements to generate an electrical signal according to X-rays emitted from an X-ray source and passing through a subject, and read the generated electrical signal as image data. These flat panel detectors have been used for generation of medical diagnostic images (in this case, X-ray absorption images) in medical practice such as hospitals. A variety of medical diagnostic imaging systems have also been developed which include FPDs, X-ray sources, and consoles.

In many medical diagnostic imaging systems, medical diagnostic images formed by the image processing apparatus (or a console serving as an image processing apparatus) from image data obtained with an FPD are output to external systems or devices (e.g., a picture archiving and communication system (PACS)) in an order appropriate for visual convenience for radiographic interpreters instead of the shoot order (see WO2011/142157, for example).

In recent years, X-ray imaging apparatuses have also been developed which are provided with Talbot interferometers or Talbot-Lau interferometers including FPDs, X-ray sources irradiating FPDs with X-rays, and a plurality of gratings (see Japanese Unexamined Patent Application Publication No. 2008-200359 and WO 2011/033798, for example). An X-ray imaging apparatus provided with a Talbot interferometer or Talbot-Lau interferometer is hereinafter referred to as "X-ray Talbot imaging apparatus". An FPD in an X-ray Talbot imaging apparatus is hereinafter referred to as an "X-ray detector" as distinguished from an FPD for normal photography, but has the same basic structure as the FPD. The FPD and X-ray detector both have a two-dimensional array of conversion elements to generate an electrical signal according to the incident X-rays.

In the X-ray Talbot imaging apparatus, the X-ray detector detects X-rays emitted from the X-ray source and passing through the subject and the gratings and reads the electrical signal generated by the conversion elements as moire image(s). The image processing apparatus reconstructs the moire image(s) into a plurality of types of medical diagnostic images, such as an absorption image, a differential phase image, and a small-angle scattering image. The reconstruction into such a plurality of types of medical diagnostic images typically requires fringe scanning or the Fourier transform.

In the case of the Fringe scanning, the X-ray Talbot imaging apparatus makes two or more X-ray exposures while moving the gratings relative to each other in order to generate two or more moire images. The image processing apparatus then reconstructs the moire image(s) into a plurality of types of medical diagnostic images, such as an absorption image, a differential phase image, and a small-angle scattering image. In the case of the Fourier transform, the X-ray Talbot imaging apparatus makes a single X-ray exposure to generate a single moire image. The image processing apparatus then analyzes and reconstructs the single moire image into a plurality of types of medical diagnostic images, such as an absorption image, a differential phase image, and a small-angle scattering image.

The medical diagnostic images (e.g., an absorption image, a differential phase image, and a small-angle scattering image) generated by both approaches show the subject in the same position because they are all reconstructed from the same moire image(s) obtained by radiographing the subject. That is, these images show the same part of the subject at the same pixel position. The medical diagnostic images show the same subject in different contrasts etc.

As in normal photography, the X-ray Talbot imaging apparatus generates one or more moire images by one or more exposures of the subject to X-rays, and the image processing apparatus reconstructs the moire image(s) into medical diagnostic images (e.g., an absorption image, a differential phase image, and a small-angle scattering image) and then may immediately output the medical diagnostic images to external systems or devices (e.g., a PACS).

The image processing apparatus does not always output such medical diagnostic images to external systems or devices immediately after the generation. In some cases, for instance, radiography is performed for the same patient's two or more parts or two or more patients, the image processing apparatus repeats reconstruction into medical diagnostic images after completion of all the radiographic processes, and then collectively outputs the medical diagnostic images to external systems or devices (e.g., a PACS).

In the latter case, if the medical diagnostic images are collectively output to external systems or devices in an order appropriate for visual convenience for radiographic interpreters as described above, the medical diagnostic images (e.g., an absorption image, a differential phase image, and a small-angle scattering image) belonging to one group based on the moire image(s) of the same part of the same patient may be output separately, mixed into medical diagnostic images of another patient, or partially lost.

This may cause a situation where a radiographic interpreter fails to interpret patient's medical diagnostic images by lack of any of the diagnostic images; cause misdiagnosis announcing the presence of a lesion in a wrong patient due to the confusion of medical diagnostic images; and cause misdiagnosis announcing the absence of a lesion in a patient who actually has the lesion.

SUMMARY OF THE INVENTION

An object of the present invention, which has been made to solve such a problem, is to provide a medical diagnostic imaging system that certainly prevents medical diagnostic images (such as an absorption image, a differential phase image, and a small-angle scattering image, based on moire image(s) taken with an X-ray Talbot imaging apparatus) from getting mixed with other medical diagnostic images or getting lost.

To solve the above-mentioned problem, according to one aspect of a preferred embodiment of the present invention, there is provided a medical diagnostic imaging system including: an X-ray Talbot imaging apparatus including: an X-ray source, a plurality of gratings, and an X-ray detector which includes a two-dimensional array of conversion elements to generate an electrical signal according to X-rays emitted one or more times from the X-ray source and passing through a subject and the gratings, and reads the electrical signal generated by the conversion elements, as one or more moire images; and an image processing apparatus to reconstruct the one or more moire images produced in the X-ray Talbot imaging apparatus into a plurality of types of medical diagnostic images, wherein the image processing apparatus classifies the medical diagnostic images generated based on the same one or more moire images into a group and outputs the group of the medical diagnostic images as a unit to an outside.

A medical diagnostic imaging system of the present invention enables collective processing and transmission of medical diagnostic images (e.g., an absorption image, a differential phase image, and a small-angle scattering image) belonging to the same group. This accurately prevents the medical diagnostic images from getting mixed with other medical diagnostic images, prevents other medical diagnostic images from getting mixed with the medical diagnostic images, and prevents partial loss of the medical diagnostic images.

This certainly prevents the situation where a radiographic interpreter fails to interpret patient's diagnostic images by lack of any of the diagnostic images; prevents misdiagnosis announcing the presence of a lesion in a wrong patient due to the confusion of medical diagnostic images; and prevents misdiagnosis announcing the absence of a lesion in a patient who actually has the lesion.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 4 illustrates an exemplary small-angle scattering image.

FIG. 5 illustrates an exemplary bone-excluded image.

FIG. 13 illustrates an improved radiographic process using an X-ray Talbot imaging apparatus conducted by two radiologists.

DESCRIPTION OF THE PREFERRED EMBODIMENTS

An embodiment of a medical diagnostic imaging system of the invention will now be described with reference to the attached drawings.

[Structure of Medical Diagnostic Imaging System]

This embodiment provides a medical diagnostic imaging system 100 including an X-ray Talbot imaging apparatus and an image processing apparatus. If a controller 19 for an X-ray Talbot imaging apparatus 1 (which will be described below referring to FIG. 3) serves as the image processing apparatus, the medical diagnostic imaging system 100 corresponds to an X-ray Talbot imaging apparatus 1.

Figure 1:
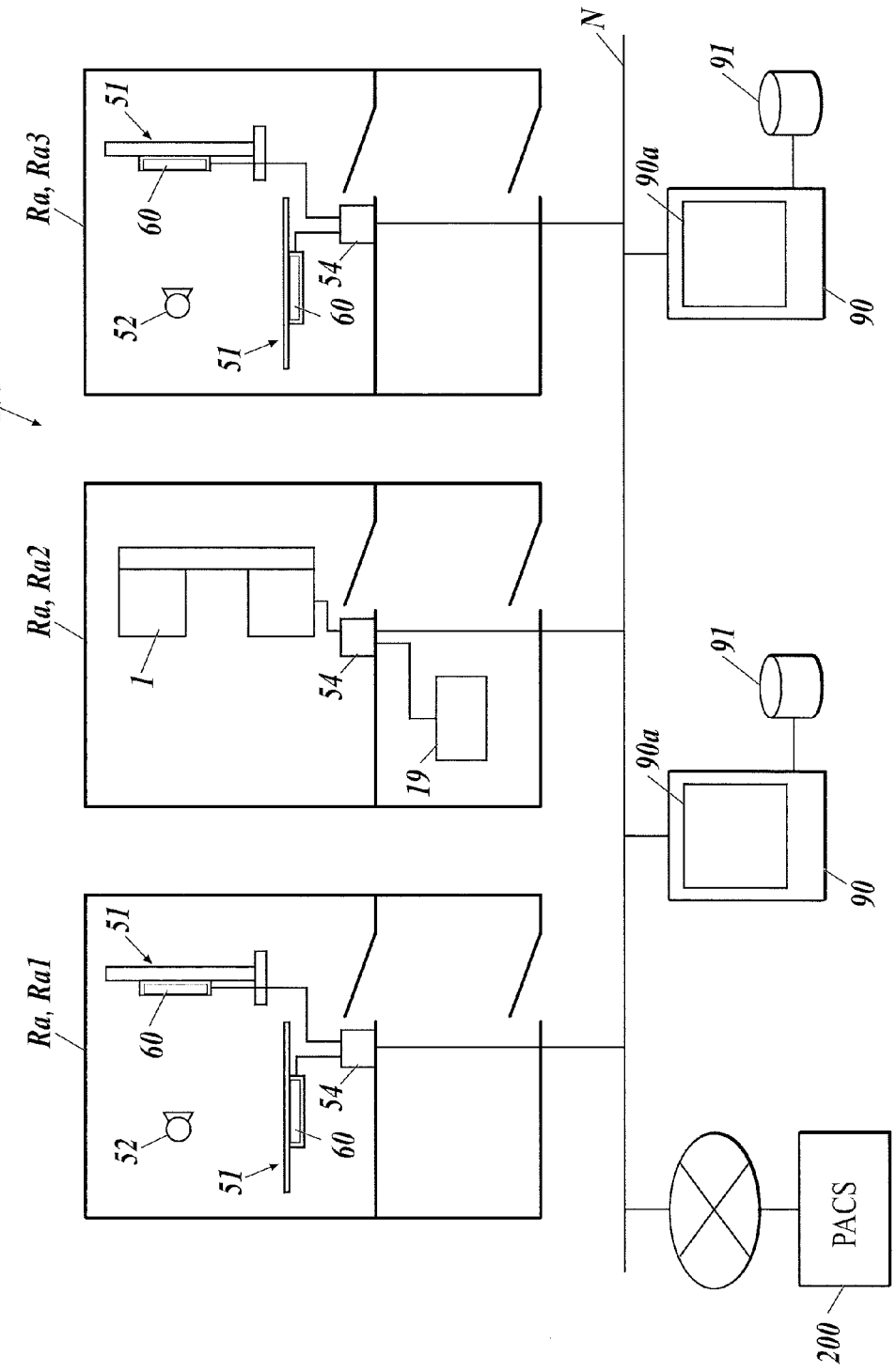
FIG. 1 illustrates an example structure of a medical diagnostic imaging system of one embodiment, including an X-ray Talbot imaging apparatus, FPDs, and consoles.

As shown in FIG. 1, the medical diagnostic imaging system 100 may further include FPDs 60, consoles 90, and other components in addition to the X-ray Talbot imaging apparatus 1. In such a case, the controller 19 for the X-ray Talbot imaging apparatus 1 or a console 90 may serve as the image processing apparatus.

Referring to FIG. 1, the medical diagnostic imaging system 100 includes radiographic chambers Ras (Ra1 to Ra3). The radiographic chambers Ra1 and Ra3 each include Bucky devices 51 to fix the FPDs 60 and an X-ray source 52 to irradiate the FPDs 60 with X-rays. The Ra2 includes the X-ray Talbot imaging apparatus 1. The radiographic chambers Ras are usually covered with lead plates to avoid leakage of X-rays. Since the lead plates interrupt direct communication between each component inside the radiographic chambers Ras and external devices, each radiographic chamber Ra is provided with a relay 54 to establish such communication.

The relays 54 are connected to the consoles 90 via a network N. The consoles 90 each include a display unit 90a and a storage unit 91. The medical diagnostic imaging system 100 may further include an irradiation device to control X-rays emitted from the X-ray sources 52, a server to collectively control data and parameters used in each console 90, and other appropriate devices. In addition, the medical diagnostic imaging system 100 is connected to a PACS 200 and other systems and devices (not shown), such as a hospital information system (HIS) and a radiology information system (RIS), via a network.

In the following description, the controller 19 for the X-ray Talbot imaging apparatus 1 serves as an image processing apparatus, which indicates that the X-ray Talbot imaging apparatus 1 itself serves as a medical diagnostic imaging system 100. Alternatively, the consoles 90 in the invention may serve as image processing apparatuses. Alternatively, the medical diagnostic imaging system 100 in the invention may include an additional image processing apparatus other than the controller 19 for the X-ray Talbot imaging apparatus 1 and the consoles 90.

In the following description, the X-ray Talbot imaging apparatus 1 is provided with a Talbot-Lau interferometer including a ray source grating (or multi-grating or multi-slit grating) 12 described later. Alternatively, the X-ray Talbot imaging apparatus 1 in the invention may be provided with a Talbot interferometer including only a first grating (or G1 grating) 14 and a second grating (or G2 grating) 15 but no ray source grating 12.

[Structure of X-Ray Talbot Imaging Apparatus]

Figure 2:
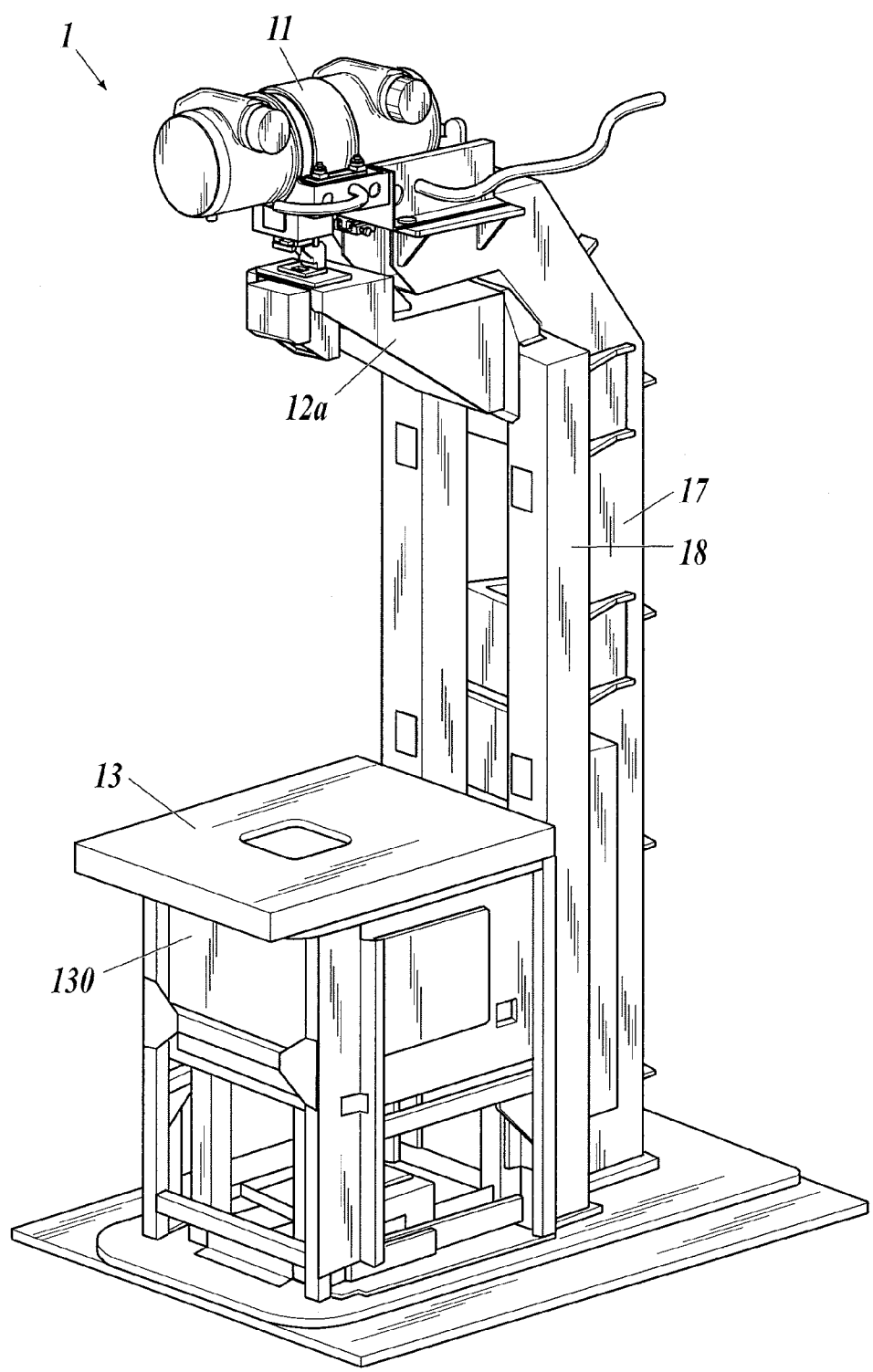
FIG. 2 is a perspective general view of the X-ray Talbot imaging apparatus of the embodiment.
Figure 3:
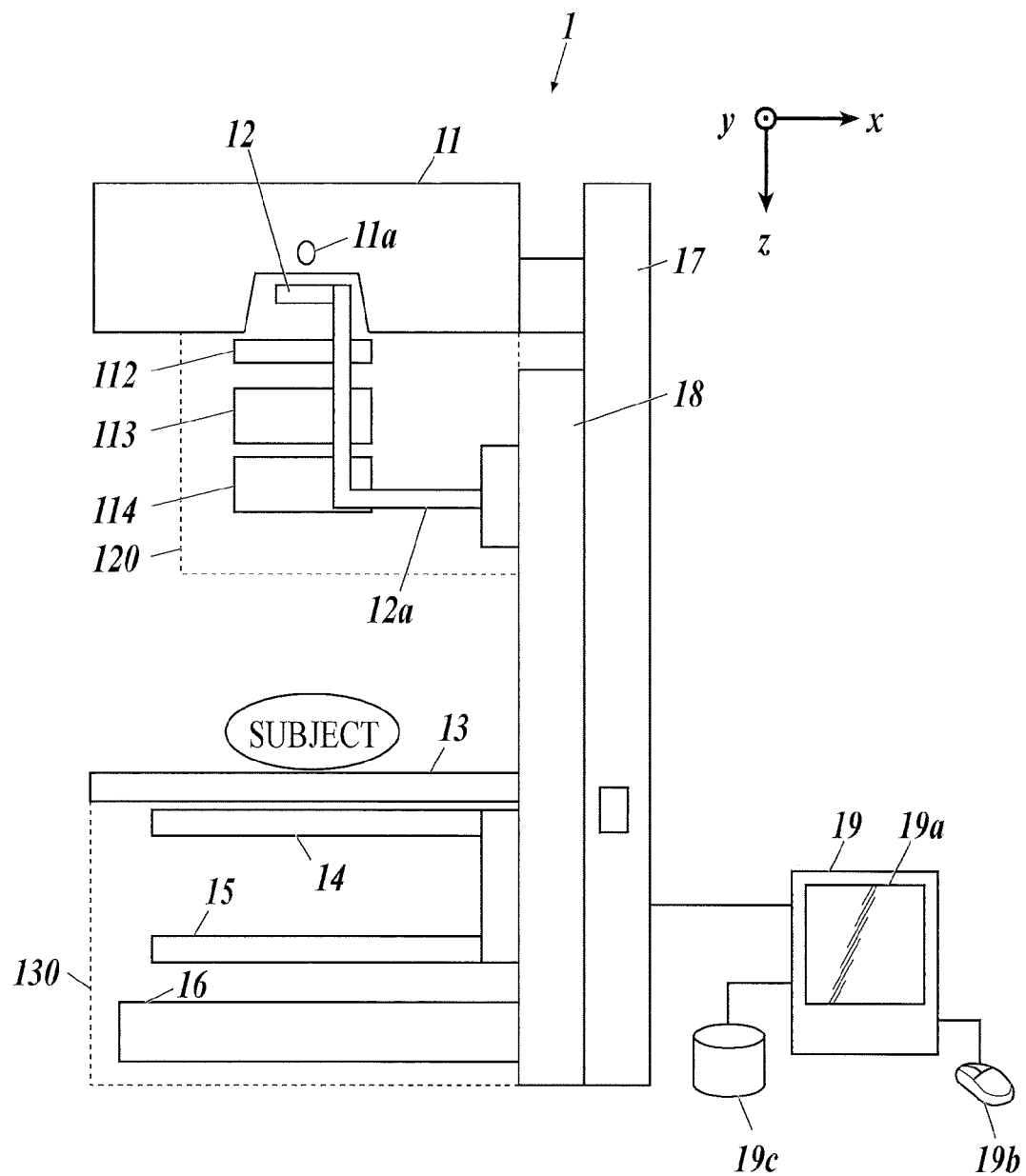
FIG. 3 is a schematic general view of the X-ray Talbot imaging apparatus of the embodiment.

The structure of the X-ray Talbot imaging apparatus of this embodiment will now be described. FIG. 2 is a perspective general view of the X-ray Talbot imaging apparatus of this embodiment. FIG. 3 is a schematic general view of the X-ray Talbot imaging apparatus of this embodiment. In this embodiment, the X-ray Talbot imaging apparatus 1 includes a radiation generator 11, a ray source grating 12, a subject table 13, a first grating 14, a second grating 15, and an X-ray detector 16.

The radiation generator 11 includes an X-ray source 11a which may be, for example, a Coolidge X-ray source, a rotating anode X-ray source, or any other source commonly used in medical practice. The ray source grating 12 is disposed below the radiation generator 11. In this embodiment, the ray source grating 12 is not mounted to the radiation generator 11 but to a fixing member 12a on the base 18 on the support 17 to prevent vibrations of the radiation generator 11 generated by the rotation of the anode of the X-ray source 11a from propagating to the ray source grating 12.

In this embodiment, the ray source grating 12, the first grating 14, and the second grating 15 have multiple slits (not shown) at regular intervals in the y direction perpendicular to the z direction parallel to the irradiation direction. In this case, the slits extend in the x direction. The fixing member 12a in this embodiment is mounted with the ray source grating 12, a filter (or additional filter) 112 to modify the quality of the radiation passing through the ray source grating 12, an irradiation field diaphragm 113 to narrow the irradiation field, and an irradiation field lamp 114 to adjust the position before the irradiation by exposing a subject to visible light instead of radiation.

The ray source grating 12, the filter 112, and the irradiation field diaphragm 113 may be positioned in any other order. A first covering unit 120 (see FIG. 3) may be provided around the ray source grating 12 and other components to protect them.

A subject table 13 is provided below the radiation generator 11 to hold a subject for radiography. The subject is a body part, especially a joint in a hand or leg of the patient. The first grating 14 and the second grating 15 are provided below the subject table 13, and the X-ray detector 16 is provided directly below the second grating 15. A second covering unit 130 is provided around the first grating 14, the second grating 15, and the X-ray detector 16 to protect them from a leg or other parts of the patient.

In this embodiment, the X-ray detector 16, which has a similar configuration as the FPD 60 as described above, includes a two-dimensional array of conversion elements (not shown) to generate an electrical signal according to X-rays emitted from the X-ray source 11a of the radiation generator 11 and passing through the ray source grating 12, the subject, the first grating 14, and the second grating 15. The X-ray detector 16 reads the electrical signal generated by the conversion elements, as a moire image.

When coherent X-rays pass through the first grating (or G1 grating) 14 with slits at regular intervals, the image of the grating is formed at regular intervals along the direction of the propagating X-rays. Such a phenomenon is known as the Talbot effect and is the principle of the Talbot interferometer or Talbot-Lau interferometer constituting the X-ray Talbot imaging apparatus 1 of this embodiment. The formed images are called self-images. The Talbot and Talbot-Lau interferometers have a second grating (or G2 grating) 15 at a location of a self-image, and forms a moire fringe on the second grating 15. A subject positioned on the subject table 13 disrupts the moire fringe. In the X-ray Talbot imaging apparatus 1, the X-ray detector 16 is configured to capture a moire image with such a moire fringe disrupted by the subject.

If the X-ray Talbot imaging apparatus 1 is configured to capture multiple moire images by fringe scanning, a transfer device (not shown) is provided therein to move any one of the ray source grating 12, the first grating 14, and the second grating 15, or both the first grating 14 and the second grating 15 in the y direction. The conversion elements in the X-ray detector 16 may be photodiodes, phototransistors, or a complementary metal oxide semiconductor (CMOS) panel.

The controller 19 for the X-ray Talbot imaging apparatus 1 is a general-purpose computer including a central processing unit (CPU), a read only memory (ROM), a random access memory (RAM), an input/output interface, and other components (not shown) connected via a bus. Alternatively, the controller 19 may be a dedicated controller. The controller 19 has a display unit 19a (e.g., a cathode ray tube (CRT) display or liquid crystal display (LCD)), an input unit 19b (e.g., a mouse and a keyboard), and an external or built-in storage unit 19c (e.g., a hard disk drive (HDD)).

The controller 19 comprehensively controls the X-ray Talbot imaging apparatus 1. For example, the controller 19 adjusts the relative positions of the first grating 14, the second grating 15, and the X-ray detector 16 of the X-ray Talbot imaging apparatus 1 and instructs the transfer device to move any one of the ray source grating 12, the first grating 14, and the second grating 15, or both the first grating 14 and the second grating 15 in the y direction. The controller 19 may also be a part of the radiation generator 11. In such a case, the controller 19 can determine the tube voltage, tube current, and irradiation time for the X-ray source 11a.

As described above, the controller 19 in this embodiment serves as an image processing apparatus that reconstructs one (in the case of the Fourier transform) or more (in the case of fringe scanning) subject's moire images (read by the X-ray detector 16) into at least three types of medical diagnostic images: an absorption image, a differential phase image, and a small-angle scattering image. "Medical diagnostic image" may hereinafter be abbreviated as "diagnostic image".

FIG. 4 shows an exemplary small-angle scattering image IV of MP joints located between metacarpals and proximal phalanxes of a forefinger, a middle finger, and a ring finger. Techniques to reconstruct one or more moire images into at least three diagnostic images: an absorption image, a differential phase image, and a small-angle scattering image are well known and therefore will not be explained in detail.

[Grouping of a Plurality of Types of Diagnostic Images]

If the X-ray Talbot imaging apparatus 1 has a setting that separately outputs a plurality of types of diagnostic images (e.g., an absorption image, a differential phase image, and a small-angle scattering image), a group of diagnostic images based on moire image(s) of the same part of the same patient may be output separately, erroneously sorted into diagnostic images of another patient, or partly lost during reconstructive generation of a plurality of types of diagnostic images by an image processing apparatus (in this embodiment, the controller 19 for the X-ray Talbot imaging apparatus 1, which is hereinafter called "image processing apparatus 19") or during transmission of these diagnostic images to other components of the medical diagnostic imaging system 100

(e.g., the console 90 (see FIG. 1)) or systems or devices external to the medical diagnostic imaging system 100 (e.g., the PACS 200).

Such a problem occurs more often in the medical diagnostic imaging system 100 provided with the FPDs 60 on the Bucky devices 51 (see FIG. 1, for example) for normal photography because not only a plurality of types of diagnostic images based on moire image(s) generated by the X-ray Talbot imaging apparatus 1 but also normal diagnostic images generated with the FPDs 60 are transmitted and received in the medical diagnostic imaging system 100 or are output to external devices.

Countermeasures to the problem in the medical diagnostic imaging system 100 of this embodiment will now be described. The advantages of the medical diagnostic imaging system 100 of this embodiment will also be explained.

In the medical diagnostic imaging system 100 of this embodiment, the image processing apparatus 19 classifies a plurality of types of diagnostic images based on a series of one or more moire images into a group, and outputs the group of diagnostic images as a unit to external systems or devices. Specifically, the image processing apparatus 19 prohibits other images (i.e., all or part of the plurality of types of diagnostic images based on other moire image(s) or diagnostic image(s) generated by normal photography with the FPD 60) from being added to the group and prohibits apart of the diagnostic images belonging to the group from being extracted.

The following explains about the image processing apparatus 19 that generates three types of diagnostic images: an absorption image IAB, a differential phase image IDP, and a small-angle scattering image IV based on a series of one or more moire images, and is also applicable to generation of other diagnostic images, e.g., a bone-excluded image IA (see FIG. 5) generated from an absorption image IAB and a differential phase image IDP based on a series of one or more moire images.

A bone-excluded image IA is generated by removing a processed absorption image IAB from a differential phase image IDP to exclude or attenuate image signals expressing the bone in the differential phase image IDP. The bone-excluded image IA visualizes cartilage or other soft parts (in FIG. 5, the metacarpal cartilage between the metacarpus and the proximal phalanx). Refer to Japanese patent application No. 2013-256561 for more details on the process of generating bone-excluded images IA.

Upon generation of three types of diagnostic images (an absorption image IAB, a differential phase image IDP, and a small-angle scattering image IV) based on a series of one or more moire images, the image processing apparatus 19 in this embodiment indicates that these three diagnostic images belong to the same group by a predetermined method, e.g., by writing a common ID in the headers of image data.

The indicated three diagnostic images IAB, IDP, and IV are collectively treated as a group G. In particular, these three diagnostic images IAB, IDP, and IV are transmittable to and processable in systems or devices external to the medical diagnostic imaging system 100 (e.g., the PACS 200), as one group G.

Figure 6A:
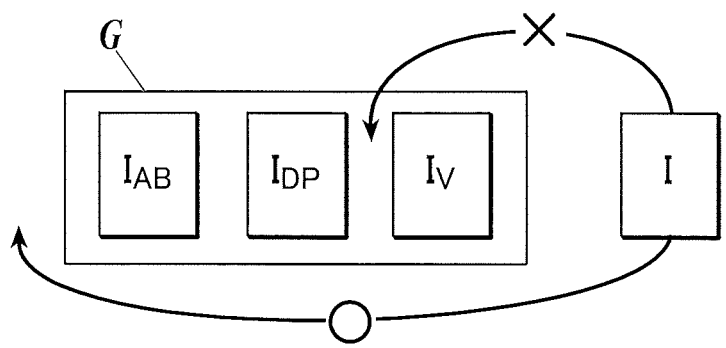
FIG. 6A shows prohibited misclassification of another medical diagnostic image to a group.
Figure 6B:
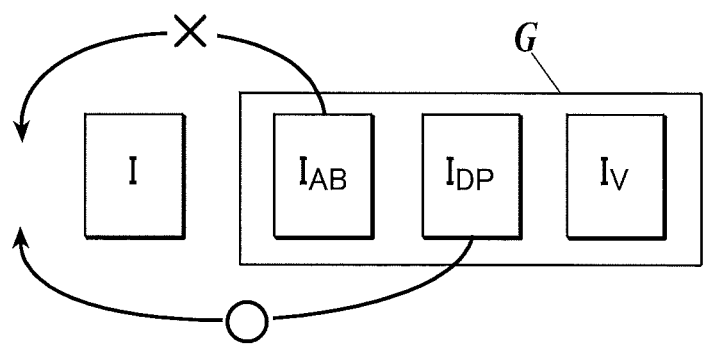
FIG. 6B shows prohibited partial extraction of the medical diagnostic images from the group.

Collective treatment of the three diagnostic images IAB, IDP, and IV as the group G is to prevent entry of another diagnostic image I (i.e., a diagnostic image generated by normal photography with the FPD 60 or a diagnostic image belonging to another group) to each group G as shown in FIG. 6A and to prevent partial extraction of the diagnostic images IAB, IDP, and IV in each group G as shown in FIG. 6B, during the above-mentioned sorting for the input/output operation.

In specific, collective treatment of the three diagnostic images IAB, IDP, and IV as the group G is to treat the group G as a single image. The absorption image IAB, differential phase image IDP, and small-angle scattering image IV in the same group G can be output or displayed in any order as appropriate.

Such a configuration allows for collective processing and transmission of the diagnostic images (e.g., absorption image IAB, differential phase image IDP, and small-angle scattering image IV) in the same group and certainly prevents any of these diagnostic images IAB, IDP, and IV from getting mixed with other diagnostic images I, prevents other diagnostic images I from getting mixed with the diagnostic images IAB, IDP, and IV, and prevents partial loss of the diagnostic images IAB, IDP, and IV.

When the image processing apparatus 19 is to perform image processing on the plurality of types of diagnostic images IAB, IDP, and IV classified as a group G, the image processing apparatus 19 can collectively apply the same image processing to all of the diagnostic images IAB, IDP, and IV belonging to the same group G.

Upon an instruction from an operator (e.g. a radiologist) to write information (e.g. a marker indicating a right or left hand and a stamp showing the patient's name) in a predetermined site of a diagnostic image in the group G (e.g. an absorption image IAB), the image processing apparatus 19 writes the information in the predetermined site of the diagnostic image and, although not instructed, also writes the same information in the same sites of the other diagnostic images (e.g. a differential phase image IDP and a small-angle scattering image IV).

Similarly, upon an instruction from the operator (e.g. a radiologist) to subject a diagnostic image in the group G (e.g. an absorption image IAB) to rotation, inversion, establishment of a region of interest (ROI), or cropping, the image processing apparatus 19 applies the specified process to the diagnostic image and, although not instructed, also applies the same process to the other diagnostic images (e.g., a differential phase image IDP and a small-angle scattering image IV).

An exemplary graphical user interface (GUI) described below can be employed for a collective process of the diagnostic images IAB, IDP, and IV in the same group G with the image processing apparatus 19. In FIGS. 7A, 7B, 8A, and 8B, "DR" denotes normal photography conducted with the FPD 60. Clicking the icon "DR" presents a single diagnostic image I on the display.

In this case, the image processing apparatus 19 presents a screen (see FIG. 7A) on the display unit 19a for the processing of the diagnostic images IAB, IDP, and IV in the same group. The icons for the diagnostic images to be output are displayed on the left of the screen. For groups G consisting of diagnostic images IAB, IDP, and IV based on moire image(s) generated with the X-ray Talbot imaging apparatus 1, an icon (shown as " . . . Talbot") is created not for each of the diagnostic images IAB, IDP, and IV but for each group G.

Figure 7A:
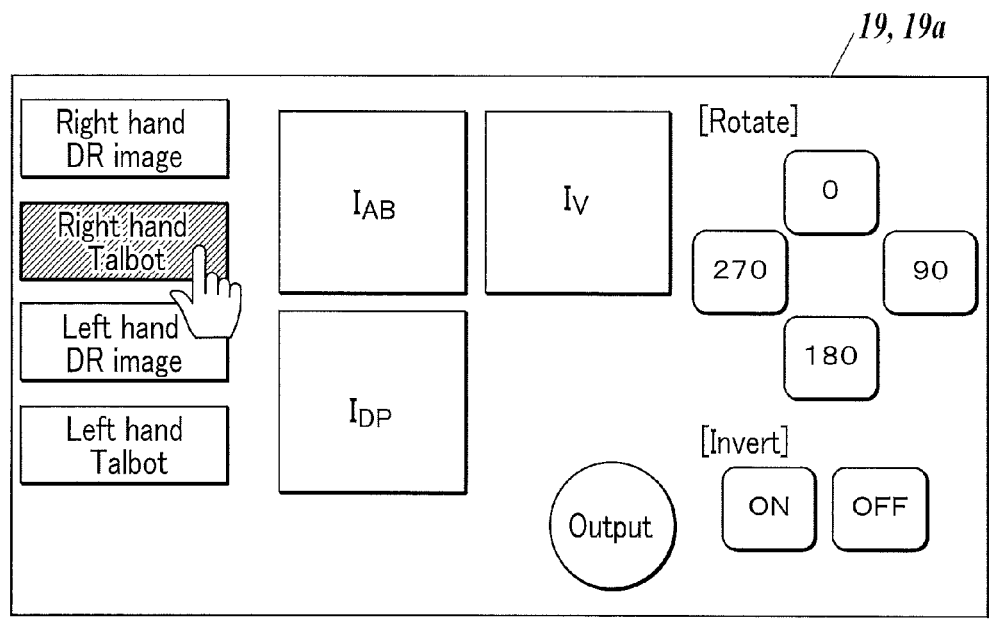
FIG. 7A illustrates a screen of a display unit showing the processing on a GUI.

As shown in FIG. 7A, clicking the icon "Right hand Talbot" causes the image processing apparatus 19 to present diagnostic images IAB, IDP, and IV in the center of the screen. In the drawing, each frame enclosing the characters (e.g. "IV") is actually a corresponding image (e.g. a small-angle scattering image IV in FIG. 4). Although not shown, clicking the icon " . . . DR" causes the image processing apparatus 19 to present a single diagnostic image I, generated by normal photography with the FPD 60, in the center of the screen. Optionally, the diagnostic images IAB, IDP, and IV in the center of the screen may be enclosed by respective frames of the same color so as to be recognized as members belonging to the same group.

Clicking the icon "Output" at the bottom of the screen causes the image processing apparatus 19 to sequentially output diagnostic images I, represented by the icons listed vertically on the left of the screen, in the top-to-bottom order of the corresponding icons. The operator (e.g., radiologist) can change the precedence (the order in which the diagnostic images I are output) by clicking and dropping the icons.

Figure 7B:
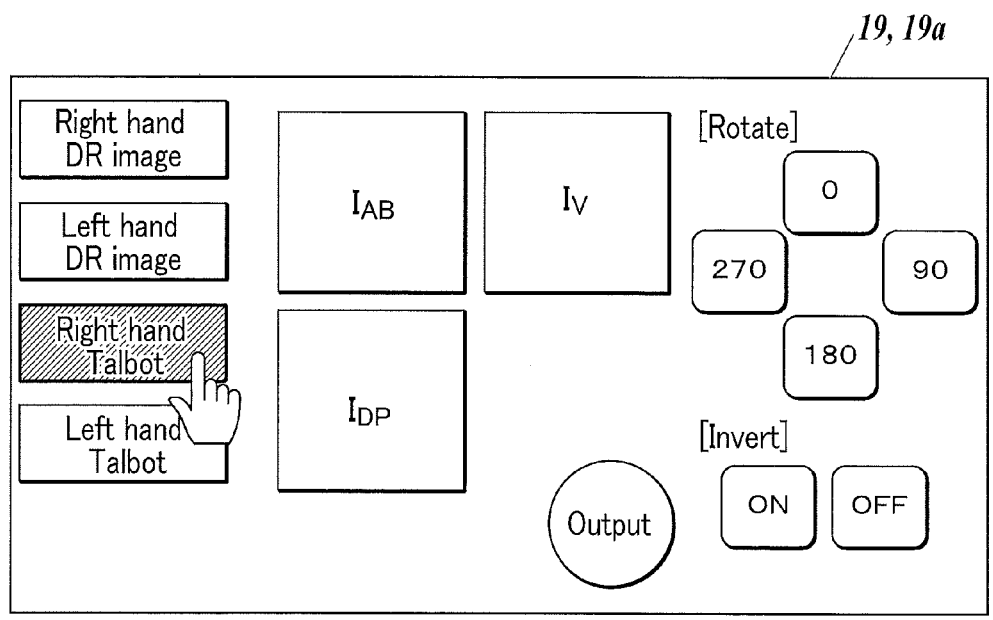
FIG. 7B shows the modification of the outputting order by clicking icons.

To output diagnostic images I represented by "Right hand Talbot" (in this case, the diagnostic images IAB, IDP, and IV) after the diagnostic image I represented by "Left hand DR image", the icon "Right hand Talbot" is clicked and dropped between the icons "Left hand DR image" and "Left hand Talbot" as shown in FIG. 7B. The order indicated in FIG. 7A can also be changed by clicking and dropping the icon "Left hand DR image" between the icons "Right hand DR image" and "Right hand Talbot".

Such a GUI displays only one icon for each group G consisting of diagnostic images IAB, IDP, and IV based on moire image(s) generated by the X-ray Talbot imaging apparatus 1, and treats the diagnostic images IAB, IDP, and IV as one icon. For instance, the GUI collectively treats diagnostic images IAB, IDP, and IV as one group G (i.e., one icon) in changing the order in which diagnostic images I are output or displayed.

The GUI thus prevents another diagnostic image I from being added to diagnostic images IAB, IDP, and IV in a group G as shown in FIG. 6A and prevents a part of the diagnostic images IAB, IDP, and IV in a group G from being extracted from the group G as shown in FIG. 6B.

Figure 8A:
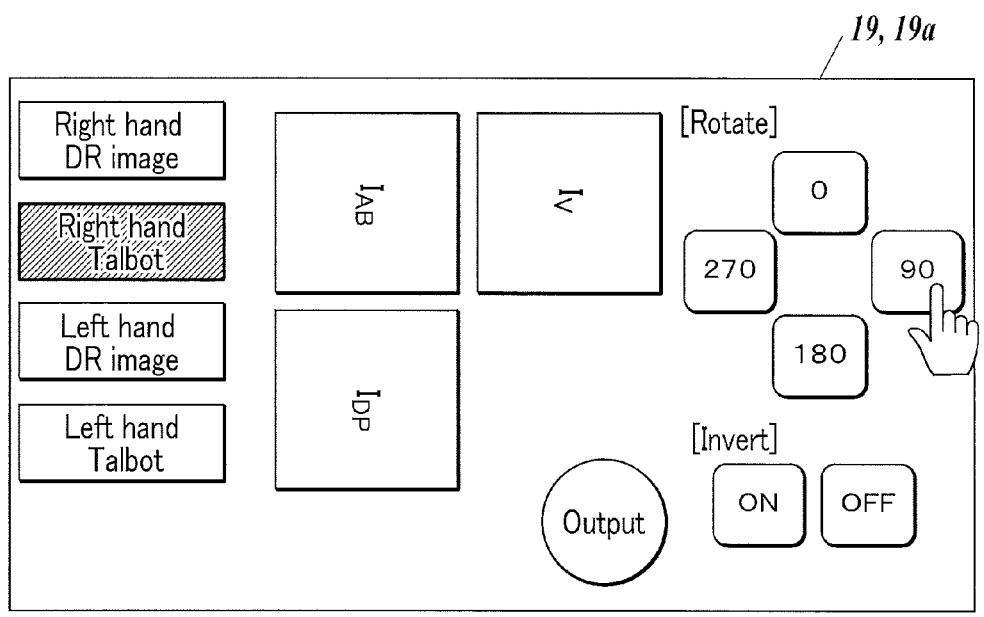
FIG. 8A shows 90° rotation of the images by clicking an icon on the GUI.

On the GUI, clicking one of the icons for rotation on the right of the screen in FIG. 8A, e.g., the icon "90" (for 90° clockwise rotation) collectively rotates the diagnostic images IAB, IDP, and IV 90° clockwise. In FIG. 8A, the laterally-turned characters "IAB" "IDP" and "IV" represent diagnostic images IAB, IDP, and IV rotated 90° clockwise in the center of the screen.

Similarly, although not shown, clicking the icon "180" (for 180° clockwise rotation) collectively rotates the diagnostic images IAB, IDP, and IV 180° clockwise and clicking the icon "270" (for 270° clockwise rotation) collectively rotates the diagnostic images IAB, IDP, and IV 270° clockwise.

Although not shown, clicking the "Invert" icon "ON" collectively inverts the diagnostic images IAB, IDP, and IV, while clicking the "Invert" icon "OFF" collectively restores the diagnostic images IAB, IDP, and IV to the original state. When information (e.g., a marker or stamp) is written, a region of interest (ROI) is specified, or cropping is performed for one of the diagnostic images IAB, IDP, and IV displayed in the screen center, the same process is also performed for the other diagnostic images without the instruction by the operator (e.g., radiologist).

The GUI allows processes on the diagnostic images IAB, IDP, and IV to be performed not separately but collectively as explained above.

Figure 8B:
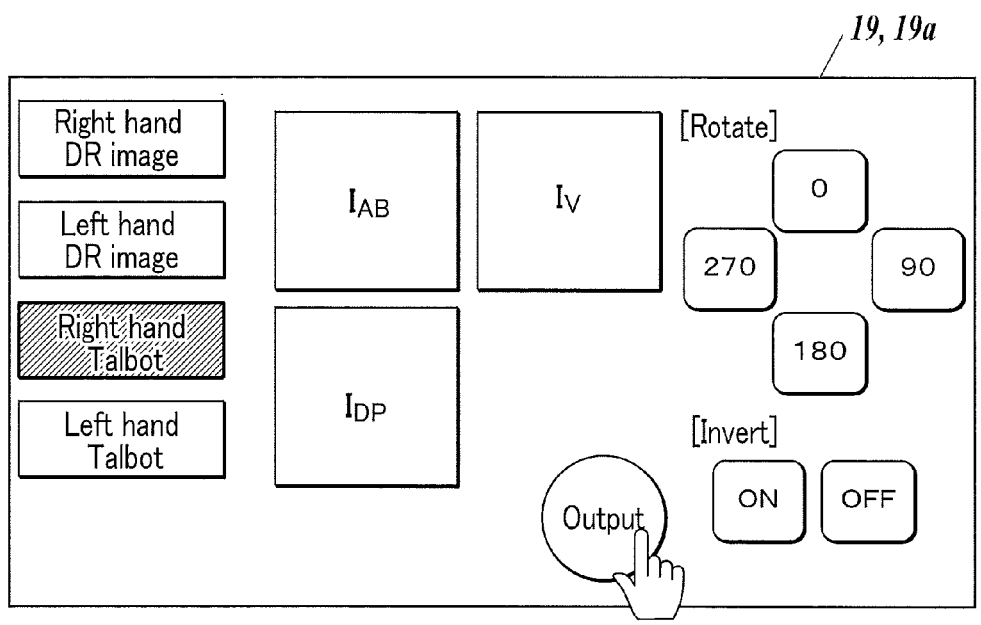
FIG. 8B shows the sequential output of the medical diagnostic images or groups by clicking an output icon.

With reference to FIG. 8B, clicking the icon "Output" at the bottom of the screen causes the image processing apparatus 19 to sequentially output diagnostic images I in the top-to-bottom order of the corresponding icons listed vertically on the left of the screen, to external systems or devices, such as PACS 200 (see FIG. 1), as explained above.

In this output operation, diagnostic images IAB, IDP, and IV based on a series of moire images generated with the X-ray Talbot imaging apparatus 1 are collectively output in the form of a group G, as explained above.

In this embodiment, the image processing apparatus 19 outputs diagnostic images I in accordance with digital imaging and communications in medicine (DICOM), a standard for medical information interchange. PACS, viewers, and other devices according to this standard also hold grouping information (e.g., common IDs in the header). Hence, diagnostic images IAB, IDP, and IV classified into the same group are collectively processed in the form of a group G even after being output from the medical diagnostic imaging system 100.

With such a configuration, devices external to the medical diagnostic imaging system 100 can also prevent other diagnostic images I from being added to each group consisting of diagnostic images IAB, IDP, and IV, and prevent partial extraction of the diagnostic images IAB, IDP, and IV in each group G. This allows for collective processing of diagnostic images IAB, IDP, and IV belonging to the same group.

[Advantageous Effects]

In the medical diagnostic imaging system 100 of this embodiment, the image processing apparatus 19 classifies diagnostic images IAB, IDP, and IV (which are based on moire image(s) generated with the X-ray Talbot imaging apparatus 1) into one group G and outputs the group of diagnostic images IAB, IDP, and IV as a unit to external systems or devices. Accordingly, a diagnostic image I in another group cannot be added to this group G, and a part of the diagnostic images IAB, IDP, and IV belonging to the group G cannot be extracted from the group G.

Such a configuration enables collective processing and transmission of diagnostic images (e.g., an absorption image IAB, a differential phase image IDP, and a small-angle scattering image IV) belonging to the same group. This accurately prevents the diagnostic images IAB, IDP, and IV from getting mixed with other diagnostic images I, prevents other diagnostic images I from getting mixed with the diagnostic images IAB, IDP, and IV, and prevents partial loss of the diagnostic images IAB, IDP, and IV.

This certainly prevents the situation where a radiographic interpreter fails to interpret patient's diagnostic images by lack of any of the diagnostic images; prevents misdiagnosis announcing the presence of a lesion in a wrong patient due to the confusion of diagnostic images; and prevents misdiagnosis announcing the absence of a lesion in a patient who actually has the lesion.

[Holder for Radiography of Knee]

The subject (patient's body) should be secured with no movement during X-ray radiation for forming one or more moire images, in a process of generating a plurality of types of diagnostic images (e.g., a differential phase image IDP) by applying Fourier analysis to a single moire image produced by a single X-ray exposure by the X-ray Talbot imaging apparatus, particularly in a process of generating a plurality of types of diagnostic images by fringe scanning which requires a plurality of types of moire images produced by a plurality of X-ray exposures by the X-ray Talbot imaging apparatus.

To radiograph a patient's finger joint, the patient should just stay seated close to the X-ray Talbot imaging apparatus 1 and stretch his hand on the subject table 13 (see FIGS. 2 and 3) with his hand and fingers fixed to a holder. Thus, the patient feels relatively comfortable during radiography. To radiograph a patient's knee joint, however, the patient should stay still on the subject table 13. Such a state precludes ready radiography.

To observe or diagnose the time-dependent change of the patient's joint, the joint should preferably be irradiated with X-rays emitted from the same direction (the angle of the joint to the direction of the X-rays should preferably be fixed) in every regular radiographic process.

This means that the patient's joint should preferably be fixed to have the same angle to the direction of the X-rays or the top surface of the subject table 13 in every radiographic process. For example, a finger joint can have the same angle in every radiographic process if it is fixed to a holder (disclosed in Japanese patent application No. 2013-189957, for example) for adjustment of the angle. A patient's knee joint, however, cannot readily be fixed at the same angle in every radiographic process.

The inventors have found after study that a patient's knee and its angle can be certainly fixed during the radiography of the knee joint by a configuration for the X-ray Talbot imaging apparatus 1 and the holder, which will be described below.

Figure 9:
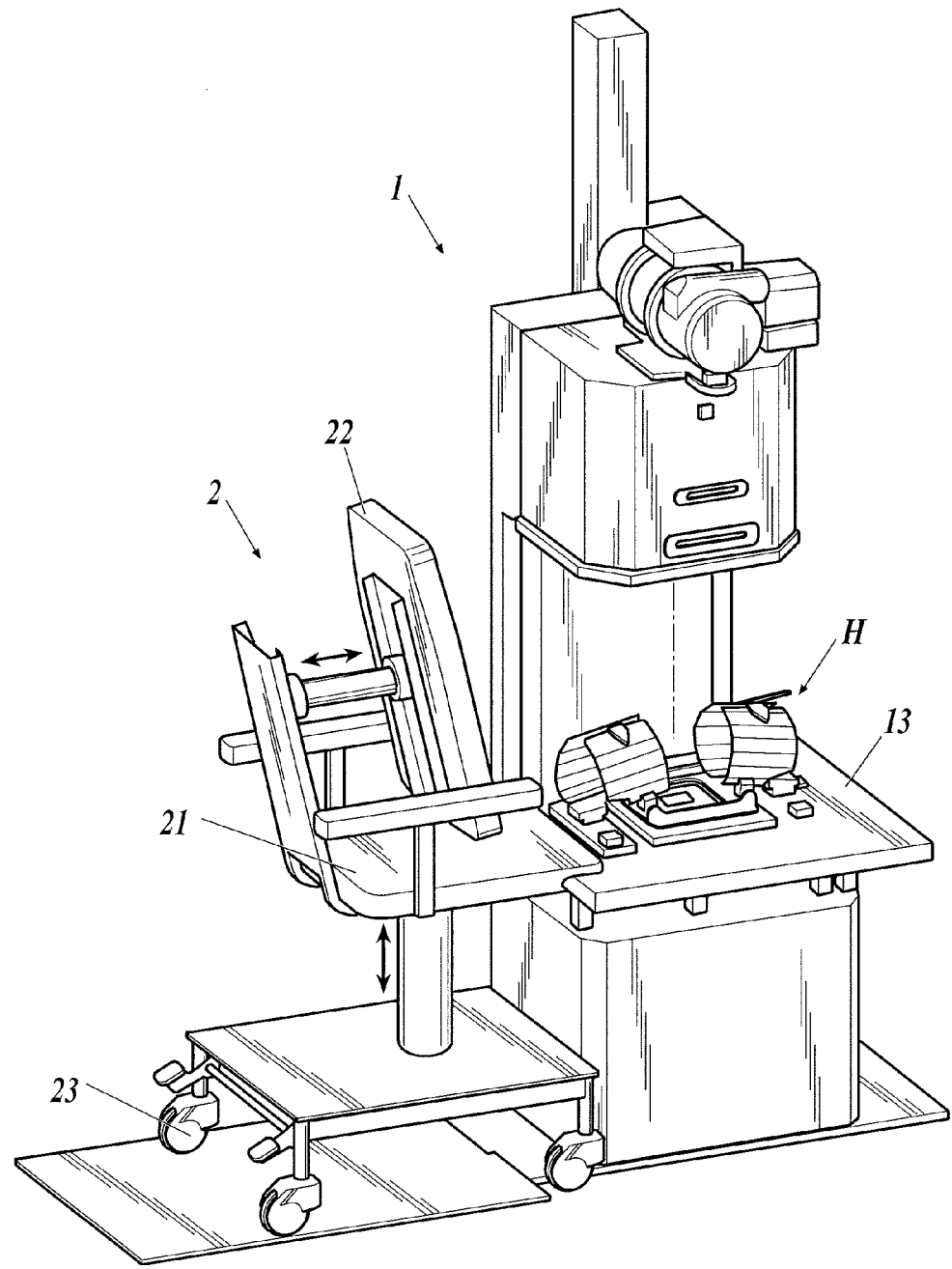
FIG. 9 is an external perspective view of the X-ray Talbot imaging apparatus during the radiography of a knee joint.

In this configuration, as shown in FIG. 9, a chair 2 is placed close to the X-ray Talbot imaging apparatus 1. The chair 2 has a vertically movable seat 21 and a forward movable backrest 22 (in this case, movable toward the X-ray Talbot imaging apparatus 1). The seat 21 has a tilting mechanism (vertically swinging about a horizontally extending shaft). The chair 2 can measure the tilt angle of the seat 21 and can also measure the vertical position of the seat 21 and the forward movement distance of the backrest 22.

The patient's knee joint is usually radiographed in the following process. The seat 21 is lowered and the backrest 22 is moved back. The patient sits in the seat 21. The seat 21 is lifted appropriately for the patient such that the top surfaces of the seat 21 and the subject table 13 of the X-ray Talbot imaging apparatus 1 flush with each other. Both of the patient's legs are placed on the subject table 13 of the X-ray Talbot imaging apparatus 1. The chair 2 with the patient thereon is brought close to or in contact with the X-ray Talbot imaging apparatus 1 and then fixed in the position such that wheels 23 of the chair 2 do not rotate.

The patient and the backrest 22 are moved forward such that the patient's knee is placed over an opening 13a (see FIG. 10) of the subject table 13 through which radiation rays pass. A target leg of the patient is fixed to a holder H and then radiographed. The opening 13a is a portion which is unshielded by lead or any other material to transmit radiation rays. The portion may be closed with a material through which radiation rays can pass.

It should be noted that this process can be modified as appropriate in accordance with the state of the patient. Another process can be applied which involves operating the seat 21 in the form of a conveyor belt while moving the backrest 22 forward so that the patient's body can be automatically moved forward with the seat 21 and the backrest 22.

Alternatively, although not shown, the seat 21 in the form of a turntable may be lifted or rotated while the patient is seated sideways to the X-ray Talbot imaging apparatus 1 to place the both legs of the patient on the subject table 13 of the X-ray Talbot imaging apparatus 1.

Referring to FIG. 9, the chair 2 is on the left of the X-ray Talbot imaging apparatus 1. Alternatively, although not shown, the chair 2 may be on the right of the X-ray Talbot imaging apparatus 1 so that the patient can throw his leg on the subject table 13 from the right. The following description, which is based on FIG. 9, is also applicable to such a situation where the chair 2 is disposed on the right of the X-ray Talbot imaging apparatus 1.

Figure 10:
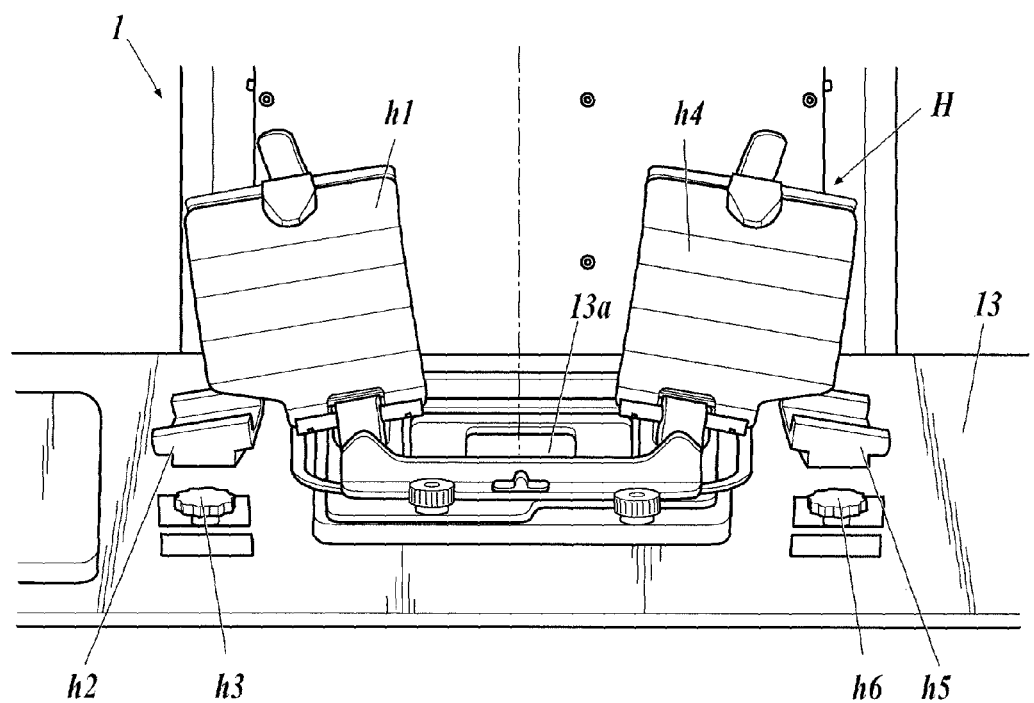
FIG. 10 is an enlarged view of a holder mounted on the subject table of the X-ray Talbot imaging apparatus in FIG. 9.

With reference to FIG. 10, the holder H is mounted on the subject table 13 of the X-ray Talbot imaging apparatus 1 and includes fasteners h1 and h4 to wrap tightly around patient's thigh and shin, respectively, for fixation, and supports h2 and h5 to support the patient's thigh and shin, respectively, from below. Turning a dial h3 changes the distance from the top surface of the subject table 13 to the fastener h1 and the support h2 for fixation of the patient's thigh. Similarly, turning a dial h6 changes the distance from the top surface of the subject table 13 to the fastener h4 and the support h5 for fixation of the patient's shin.

As such, the configuration adjusts the vertical position of the seat 21 and tilts the seat 21 to adjust the vertical angle of the patient's thigh. Concurrently, the configuration adjusts the angles of the fastener h1 and the support h2 for fixation of the patient's thigh and the distance from the top surface of the subject table 13 to the fastener h4 and the support h5 for fixation of the patient's shin. Thus, the configuration can adjust the angle of the patient's knee, i.e., the angle of the knee joint to the direction of X-rays emitted from the above with reference to FIG. 10.

The patient may feel pain when his thigh and shin are directly wrapped tightly with the fasteners h1 and h4. Loosening the fasteners h1 and h4 to avoid such a problem, however, may lead to unintentional movement of the patient's leg in the fasteners h1 and h4. To address such a problem, the patient's leg to be radiographed is preferably wrapped with a holding cushion h7 in FIG. 11A and then with the fasteners h1 and h4.

Figure 11A:
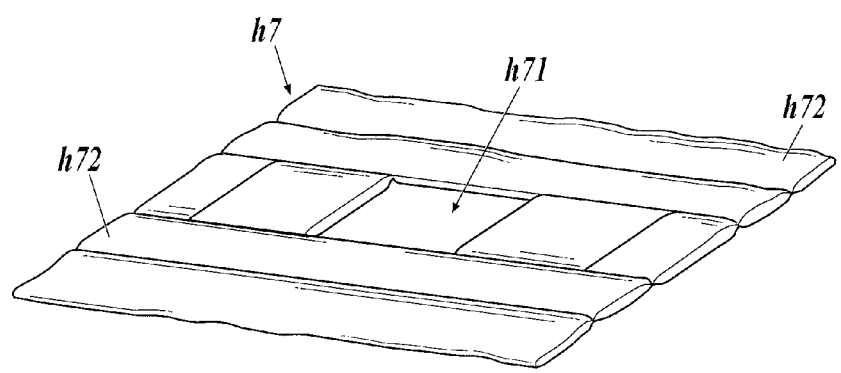
FIG. 11A illustrates the structure of a holding cushion.

As shown in FIG. 11A, the holding cushion h7 may be a vacuum cushion with an opening h71 in the center. The holding cushion h7 consists of more than one rectangular bladders h72 combined to form a sheet with the opening h71 in the center. Each bladder h72 is in partial communication with the adjacent bladder h72 so that the air in each bladder h72 can move into the adjacent bladder h72. Although not shown, one or more bladders h72 may be provided with a hose attached to a pump that can suck the air out of all the bladders h72 forming the holding cushion h7 via the hose.

Although not shown, each bladder h72 contains a large number of microspheres of urethane foam or any other resin. The microspheres in each bladder h72 cannot migrate into the other bladders h72.

Figure 11B:
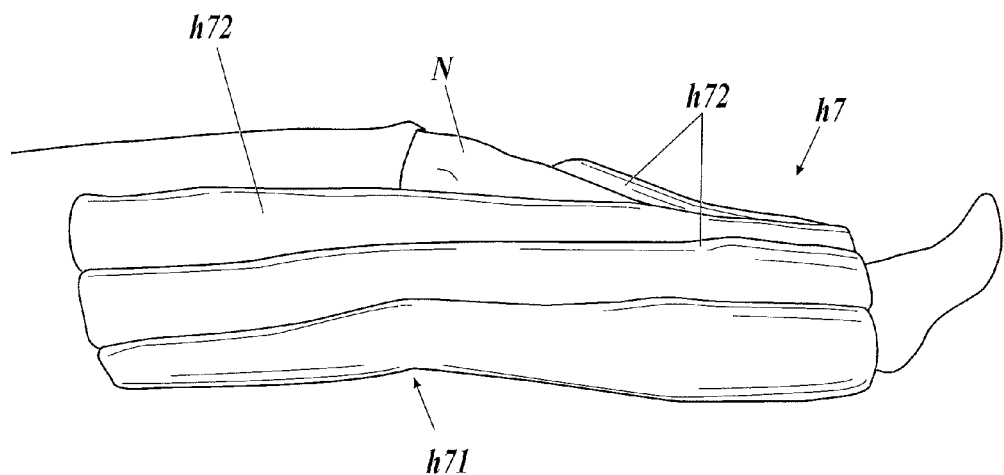
FIG. 11B illustrates the holding cushion wrapping around the patient's leg.

As shown in FIG. 11B, before the patient's leg is secured with the fasteners h1 and h4 on the subject table 13, the holding cushion h7 is positioned such that the opening h71 of the holding cushion h7 is disposed below the patient's knee N. Edges of the holding cushion h7 (which are, in the drawing, the edges farther and closer to the viewer) are lifted to wrap around the patient's leg. The microspheres in the bladders h72 filled with air can freely move in response to the movement of the holding cushion h7. When the edges of the holding cushion h7 are lifted, the holding cushion h7 can readily deform and fit to the patient's leg due to the movement of the microspheres in the bladders h72.

Although not shown in FIG. 11B, the patient's other leg (which is not the target of radiography) is placed on the subject table 13 to be substantially parallel to the radiography-target leg and is covered with an X-ray shield (containing lead or any other material) for protection from X-rays.

The pump sucks the air out of the holding cushion h7, i.e., the bladders h72. Without the air in the bladders h72 after the suction, the microspheres have no space to move therein, inhibiting deformation of the bladders h72. Thus, the patient's leg is fixed with the holding cushion h7.

The patient's leg fixed with the holding cushion h7 is further secured with the fasteners h1 and h4 (see FIG. 10). Consequently, the patient's leg can be tightly wrapped via the holding cushion h7 without causing a patient's pain and firmly secured with the fasteners h1 and h4, preventing body movement during radiography.

The configuration in FIGS. 9 to 11B thus firmly fixes the position and angle of the leg of the patient on the subject table 13 during radiography of knee joint, leading to accurate radiography without body movement.

The configuration employs the same conditions (e.g., the vertical position and tilt angle of the seat 21, the forward movement distance of the backrest 22, and the distance from the top surface of the subject table 13 to each of the fasteners h1 and h4 and each of the supports h2 and h5) for every radiographic process to readily and firmly fix the patient's knee at the same angle. Consequently, the joint can be irradiated with X-rays emitted from the same direction (the angle of the joint to the direction of the X-rays is fixed) in every regular radiographic process, so that the time-dependent change of the patient's joint can be observed or diagnosed.

With the configuration, the operator (e.g., radiologist) may record the conditions (e.g., the vertical position and tilt angle of the seat 21, the forward movement distance of the backrest 22, and the distance from the top surface of the subject table 13 to each of the fasteners h1 and h4 and each of the supports h2 and h5). Alternatively, the conditions may be automatically recorded with the X-ray Talbot imaging apparatus 1, the chair 2, or any other component.

The configuration uses the holding cushion h7 in the form of a single-piece vacuum cushion to integrally wrap the patient's thigh and shin as shown in FIGS. 11A and 11B, but may instead use separate holding cushions h7 to separately wrap the patient's thigh and shin. The configuration employs fasteners h1 and h4 (see FIG. 10, for example) separate from the holding cushion h7 (see FIG. 11A, for example), but may instead employ the fasteners h1 and h4 each having the holding cushion h7 inside so that the patient's leg inserted in the fasteners h1 and h4 can be automatically held with the holding cushion h7. Alternatively, the holding cushion h7 may be a mattress or any other thing.

[Reduction of Radiographic Time]

Figure 12:
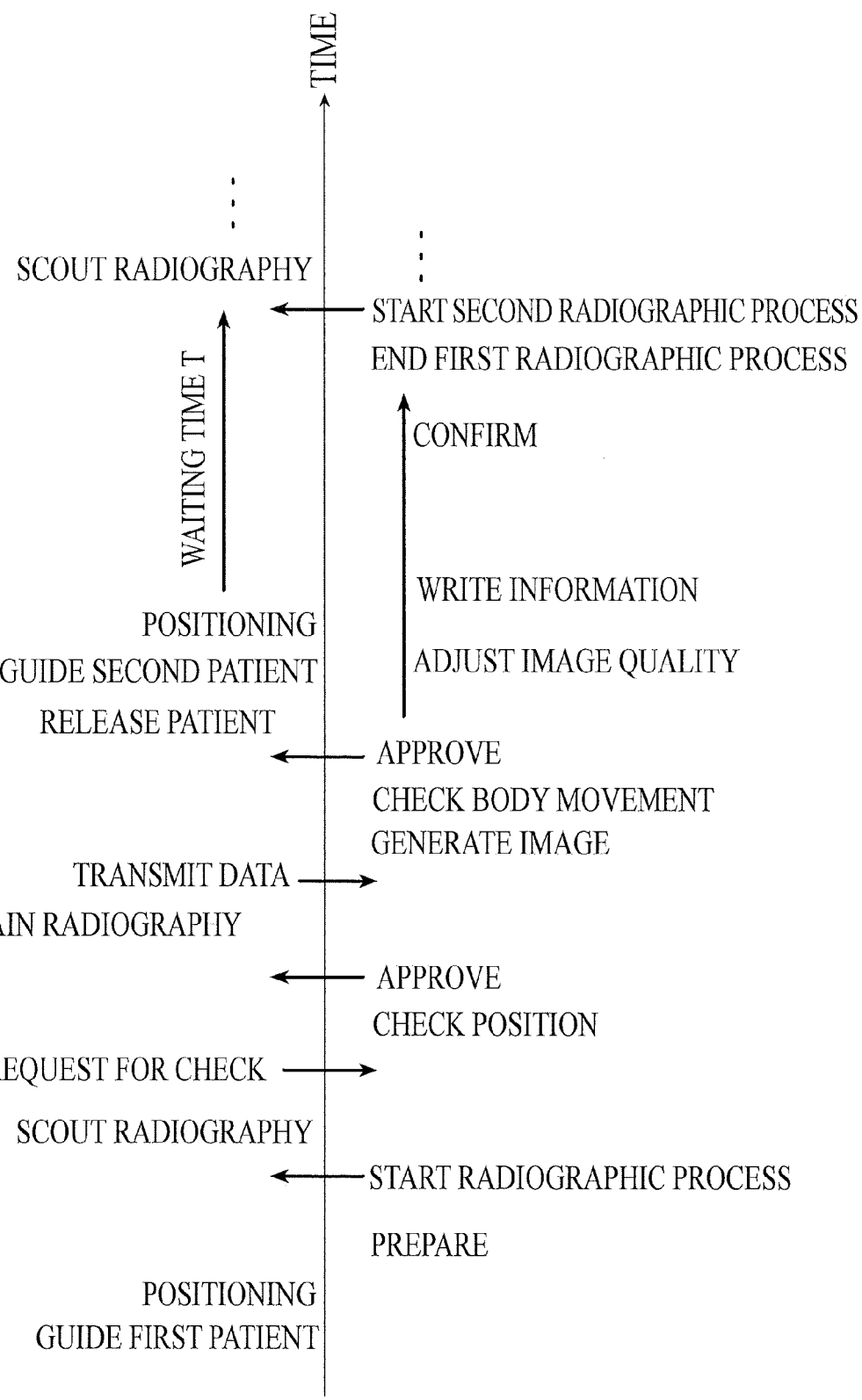
FIG. 12 illustrates a typical radiographic process using an X-ray Talbot imaging apparatus conducted by two radiologists.

The process requires two radiologists in some cases. One guides the patient and conducts a positioning process including wrapping the patient's leg with the holding cushion h7 for fixation to the holder H. The other creates diagnostic images with the image processing apparatus 19. FIG. 12 illustrates a typical radiographic process using the X-ray Talbot imaging apparatus 1, where the former is a radiologist A and the latter is a radiologist B.

The radiologist A guides the patient into the radiographic chamber Ra (see FIG. 1). To radiograph the patient's knee joint, the radiologist A sits the patient on the chair 2, lifts the seat 21, moves the chair 2, moves the backrest 22 forward, and adjusts the tilt angle of the seat 21. The radiologist A then performs a positioning process including fixing the patient's leg to the holder H and adjusting the distance from the top surface of the subject table 13 to each of the fasteners h1 and h4 and other components.

The radiologist B in the operation or preparatory room of the radiographic chamber Ra powers on the image processing apparatus 19 and performs preparation. After the pretreatment, the radiologist B instructs the radiologist A in the radiographic chamber Ra to start radiography (i.e., tells the radiologist A that the preparation is completed and the radiography can be started).

Upon reception of the instruction to start the radiography, the radiologist A in the radiographic chamber Ra operates the X-ray Talbot imaging apparatus 1 to emit weak X-rays from the X-ray source 11a (see FIG. 3, for example) for scout radiography, and then sends the radiologist B in the operator room a request to check the obtained moire image. The radiologist B checks the scout moire image to see if the target part of the patient (e.g., knee joint) is located in an appropriate position in the moire image and, if necessary, then instructs the radiologist A in the radiographic chamber Ra to correct the position. The radiologist B approves the position if the target part is located in an appropriate position in the moire image.

After the position is approved, the radiologist A in the radiographic chamber Ra performs main radiography. The X-ray source 11a of the X-ray Talbot imaging apparatus 1 emits a predetermined dose of X-rays once (for use of the Fourier transform), or more times with any of the gratings at different positions (for use of fringe scanning). Upon completion of the main radiography, the X-ray Talbot imaging apparatus 1 transmits the data of the resulting moire image(s) to the image processing apparatus 19.

The radiologist B in the operator room produces an absorption image IAB, a differential phase image IDP, and a small-angle scattering image IV based on the received moire image(s). In this process, the radiologist B checks the produced images for the body movement of the patient made in the radiography, before adjusting the quality of the images.

The study of the inventors shows that body movement appears more clearly in small-angle scattering images IV than absorption images IAB and differential phase images IDP. It is thus preferred to first produce a small-angle scattering image IV and present it on the display unit 19a during such a step of producing images based on the moire image(s) from the X-ray Talbot imaging apparatus 1. This advantageously shortens the time for checking of body movement because the radiologist B can check it upon generation of only the small-angle scattering image IV instead of all the absorption image IAB, the differential phase image IDP, and the small-angle scattering image IV.

If the radiologist B finds any body movement, the radiologist A in the radiographic chamber Ra performs another main radiography. If the radiologist B finds no body movement and gives approval, the radiologist A in the radiographic chamber Ra unfastens the holder H to release the patient and terminates the radiography of the patient. The radiologist A then guides the next patient and performs the same positioning process.

If finding no body movement and giving the approval, the radiologist B in the operator room produces other appropriate images (e.g., an absorption image IAB and a differential phase image IDP) in addition to the small-angle scattering image IV if not yet produced, adjusts the quality of the images to generate diagnostic images, and then writes necessary information (e.g. a marker indicating a right or left hand and a stamp showing the patient's name) in a predetermined site of the diagnostic images. When the radiologist B writes necessary information in a predetermined position in one diagnostic image with the GUI (see FIG. 7A, for example), the same information is automatically written in the same position in the other diagnostic images, increasing the work efficiency.

Upon completion of generation of the diagnostic images (e.g., an absorption image IAB, a differential phase image IDP, and a small-angle scattering image IV), the radiologist B confirms the diagnostic images (i.e., a confirmation process) and then transmits the diagnostic images (classified into groups as described above) to appropriate systems or devices (e.g., the PACS) at an appropriate timing, for example, after completion of all the radiographic processes.

Upon completion of at least the confirmation process, and the image-quality adjustment and information writing as needed (i.e., upon completion of the radiographic process), the radiologist B in the operator room instructs the radiologist A in the radiographic chamber Ra to start the next radiographic process.

This is a typical radiographic process using the X-ray Talbot imaging apparatus 1 and involving two radiologists A and B. Unfortunately, as shown in FIG. 12, the radiologist A in the radiographic chamber Ra and the second patient should wait after a positioning process, while the radiologist B in the operator room operates the image processing apparatus 19 for image-quality adjustment and information writing in the diagnostic images of the first patient.

With reference to FIG. 12, the radiologist A in the radiographic chamber Ra and the second patient should wait for a time T after the positioning process until the end of the process in the operation room, extending the radiographic time for the second patient. This decreases the efficiency during radiography and increases the burdens on the second patient.

To solve such a problem, during the radiographic process for the first patient, information writing (e.g., markers and stamps) in images and other possible works may be started before the main radiography (see FIG. 13).

If the radiologist B in the operator room checks and approves the subject's position in the scout moire image(s) received from the radiologist A (in the radiographic chamber Ra), the position of the subject in the main radiographic image(s) is exactly or substantially the same as that in the scout moire image(s). Thus, upon the approval of the scout radiography, the radiologist B in the radiographic chamber can preliminarily determine the position and format for writing necessary information (e.g., a marker and a stamp) in diagnostic images to be produced later based on the scout moire image(s). Upon generation of the diagnostic images, the radiologist B can immediately write necessary information therein and confirm the diagnostic images.

This solution thus shortens the time period between the approval of the scout radiography and the end of the confirmation process of the diagnostic images, reducing the waiting time T between the completion of the positioning process (by the radiologist A in the radiographic chamber Ra) and the scout radiography. To radiograph some subjects such as the patient's knee joint, the positioning process requires a longer time. In this case, the radiologist B in the operator room can complete the confirmation process of the diagnostic images for the first patient before the radiologist A in the radiographic chamber Ra finishes the positioning process, in which case no waiting time T is required before the scout radiography.

As described above, the waiting time T between the completion of the positioning process for the second patient and the scout radiography can be reduced or eliminated by starting the information writing (e.g., markers and stamps) in images and other possible works before the main radiography during the radiographic process for the first patient, thereby reducing the radiographic time for the second patient. This enhances the efficiency during the radiography and certainly prevents burdens on the second patient due to excessive waiting time.

It should be understood that the present invention is not limited to the above embodiment and various modifications can be made without departing from the spirit of the invention.

The entire disclosure of Japanese Patent Application No. 2014-079211 filed on Apr. 8, 2014 including description, claims, drawings, and abstract are incorporated herein by reference in its entirety.

Although various exemplary embodiments have been shown and described, the invention is not limited to the embodiments shown. Therefore, the scope of the invention is intended to be limited solely by the scope of the claims that follow.

What is claimed is:

1. A medical diagnostic imaging system comprising:
an X-ray Talbot imaging apparatus comprising:
   an X-ray source,
   a plurality of gratings, and
   an X-ray detector which includes a two-dimensional array of conversion elements to generate an electrical signal according to X-rays emitted one or more times from the X-ray source and passing through a subject and the gratings, and reads the electrical signal generated by the conversion elements, as one or more moire images; and
an image processing apparatus to reconstruct the one or more moire images produced in the X-ray Talbot imaging apparatus into a plurality of types of medical diagnostic images, wherein
the image processing apparatus classifies the medical diagnostic images generated based on the same one or more moire images into a group, and outputs the group of the medical diagnostic images to an outside as a group to which another medical diagnostic image is prohibited from being added and from which a part of the medical diagnostic images belonging to the group is prohibited from being extracted.

2. The medical diagnostic imaging system according to claim 1, wherein the image processing apparatus is to perform image processing on the medical diagnostic images classified into the group, the image processing apparatus collectively applies the same image processing to all of the medical diagnostic images belonging to the same group.

3. The medical diagnostic imaging system according to claim 1, wherein the image processing apparatus is to delete the medical diagnostic images classified into the group, the image processing apparatus collectively deletes all of the medical diagnostic images belonging to the same group.

4. The medical diagnostic imaging system according to claim 1, wherein the medical diagnostic imaging system is further configured to first generate a small-angle scattering image IV and display the small-angle scattering image IV prior to generating a full set of images.

* * * * *